(12) United States Patent
Peltz et al.

(10) Patent No.: US 8,416,554 B2
(45) Date of Patent: Apr. 9, 2013

(54) MULTI-PHASE DECONTAMINATION OF AIRCRAFT CABIN INTERIOR

(75) Inventors: Leora Peltz, Pasadena, CA (US); Shawn H. Park, Cerritos, CA (US); John E. Kuhn, Huntington Beach, CA (US)

(73) Assignee: The Boeing Company, Chicago, IL (US)

( * ) Notice: Subject to any disclaimer, the term of this patent is extended or adjusted under 35 U.S.C. 154(b) by 49 days.

(21) Appl. No.: 13/095,563

(22) Filed: Apr. 27, 2011

(65) Prior Publication Data

US 2012/0273584 A1 Nov. 1, 2012

(51) Int. Cl.
*B05B 5/03* (2006.01)
*A61L 9/22* (2006.01)

(52) U.S. Cl. ............ 361/227; 361/228; 422/4; 422/22

(58) Field of Classification Search .......... 361/227, 361/228; 422/4, 22
See application file for complete search history.

(56) References Cited

U.S. PATENT DOCUMENTS

| | | | |
|---|---|---|---|
| 5,387,403 A * | 2/1995 | Ikeuchi et al. | 422/292 |
| 5,648,046 A * | 7/1997 | Weibel | 422/4 |
| 6,279,589 B1 | 8/2001 | Goodley | |
| 6,991,532 B2 | 1/2006 | Goldsmith | |
| 7,011,044 B2 * | 3/2006 | Segura Jobal | 119/671 |
| 7,959,859 B2 * | 6/2011 | Sparks et al. | 422/28 |
| 2005/0074359 A1 | 4/2005 | Krieger et al. | |
| 2011/0171065 A1 * | 7/2011 | Park et al. | 422/33 |

FOREIGN PATENT DOCUMENTS

| | | |
|---|---|---|
| CN | 2834546 Y | 11/2006 |
| JP | 2007283231 A | 11/2007 |
| WO | 03080132 A1 | 10/2003 |
| WO | 2007109401 A2 | 9/2007 |
| WO | 2009040684 A1 | 4/2009 |
| WO | 2011139300 A2 | 11/2011 |

OTHER PUBLICATIONS

Chen, X. et al.; Comparison of Different Decontaminant Delivery Methods for Sterilizing Unoccupied Commercial Airliner Cabins; Building and Environment; vol. 45; Issue 9; pp. 2027-2034.
International Search Report and Written Opinion of PCT/US2012/030678; May 7, 2012; 12 pages.

* cited by examiner

*Primary Examiner* — Rexford Barnie
*Assistant Examiner* — Zeev V Kitov
(74) *Attorney, Agent, or Firm* — Armstrong Teasdale LLP

(57) ABSTRACT

A method and system are provided for decontaminating at least a portion of an object. A misting device is configured to discharge a cloud formed from a plurality of cloud droplets. At least some of the cloud droplets include a decontaminating agent. A spraying device is configured to discharge a stream including a plurality of stream droplets into the cloud. At least some of the stream droplets have an electrostatic charge. At least some of the cloud droplets are deposited on the portion of the object to facilitate decontaminating the portion.

18 Claims, 4 Drawing Sheets

MULTI-PHASE DECONTAMINATION OF AIRCRAFT CABIN INTERIOR

BACKGROUND

The present disclosure relates generally to decontamination dispersion systems and, more particularly, to methods and systems for use in decontaminating an interior environment.

During operation, at least some known aircraft cabins may be exposed to pathogens. As such, at least some known aircraft cabins are commonly cleaned with decontaminations systems. At least one known decontamination system discharges a fog formed from a large amount of small droplets. Although an effective dispersion system, such fog droplets tend to condensate and/or drip, and thus increase a possibility of corrosion, bleaching, and/or impact on electronic materials, insulation, and/or fabric. Moreover, fog droplets do not typically spread over large volumes and tend to remain floating in the air for an extended duration of time before depositing on a surface.

Another known decontamination system discharges fluid through a high-voltage electronic field to electrically charge the droplets. The charged droplets do not typically penetrate into crevices, but rather, because of the charge, some droplets tend to bounce back from an opening of the crevice rather than penetrating the opening. Other known decontamination systems discharge fluid non-uniformly such that at least some parts are soaked with decontaminating fluid while other parts remain dry and/or receive little or no decontaminating agents. Discharging more decontaminating agents than is necessary to decontaminate an aircraft cabin may have an undesired effect on the portion of the aircraft cabin receiving the surplus of agents. However, attempting to uniformly discharge decontaminating fluid throughout the aircraft cabin may be tedious and/or time consuming.

BRIEF DESCRIPTION

In one aspect, a method is provided for decontaminating at least a portion of an object. The method includes discharging a cloud formed from a plurality of cloud droplets in a vicinity of the object. At least some of the cloud droplets include a decontaminating agent. A stream including a plurality of stream droplets are discharged into the cloud. At least some of the stream droplets have an electrostatic charge. At least some of the cloud droplets are deposited on the portion of the object to facilitate decontaminating the portion.

In another aspect, a system is provided for use in decontaminating at least a portion of an object. The system includes a misting device and a spraying device. The misting device is configured to discharge a cloud formed from a plurality of cloud droplets. At least some of the cloud droplets include a decontaminating agent. The spraying device is configured to discharge a stream including a plurality of stream droplets into the cloud. At least some of the stream droplets have an electrostatic charge. At least some of the cloud droplets are deposited onto the portion of the object to facilitate decontaminating the portion.

The features, functions, and advantages described herein may be achieved independently in various embodiments of the present disclosure or may be combined in yet other embodiments, further details of which may be seen with reference to the following description and drawings.

Although specific features of various embodiments may be shown in some drawings and not in others, this is for convenience only. Any feature of a drawing may be referenced and/or claimed in combination with any feature of any other drawing.

DETAILED DESCRIPTION

The subject matter described herein relates generally to decontamination systems and, more particularly, to methods and systems for use in decontaminating an interior environment. In one embodiment, a cloud of droplets are discharged from a decontamination system into an aircraft cabin. After a predetermined amount of time, the decontamination system then discharges a stream of electrically-charged droplets into the cloud of droplets. The electrically-charged droplets attract the cloud droplets towards a surface of the aircraft cabin to facilitate enhancing the decontamination of the aircraft cabin. As such, the decontamination system described herein enables areas having complex geometries to be decontaminated.

While the following description references an aircraft, it should be appreciated that the subject matter described herein may be applicable to the decontamination of any area. For example, the subject matter described herein could just as readily be applied to the decontamination of a vehicle, a building, and/or any other area that is at least potentially contaminated. Accordingly, any reference to "aircraft" throughout the following description is merely meant to illustrate one potential application of the teachings of the subject matter described herein.

As used herein, the term "decontaminating" refers to removing, inactivating, and/or destroying a pathogen on a surface and/or item such that the pathogen is no longer capable of transmitting infectious particles and such that the surface and/or item is rendered safe for handling, use, and/or disposal. The term "pathogen" refers to any disease, illness, and/or infection-producing agent including, without limitation, a germ, a virus, a bacterium, a protozoon, a fungus, and/or a microorganism.

As used herein, an element or step recited in the singular and proceeded with the word "a" or "an" should be understood as not excluding plural elements or steps unless such exclusion is explicitly recited. Furthermore, references to "one embodiment" of the present invention or the "exemplary embodiment" are not intended to be interpreted as excluding the existence of additional embodiments that also incorporate the recited features.

Figure 1:
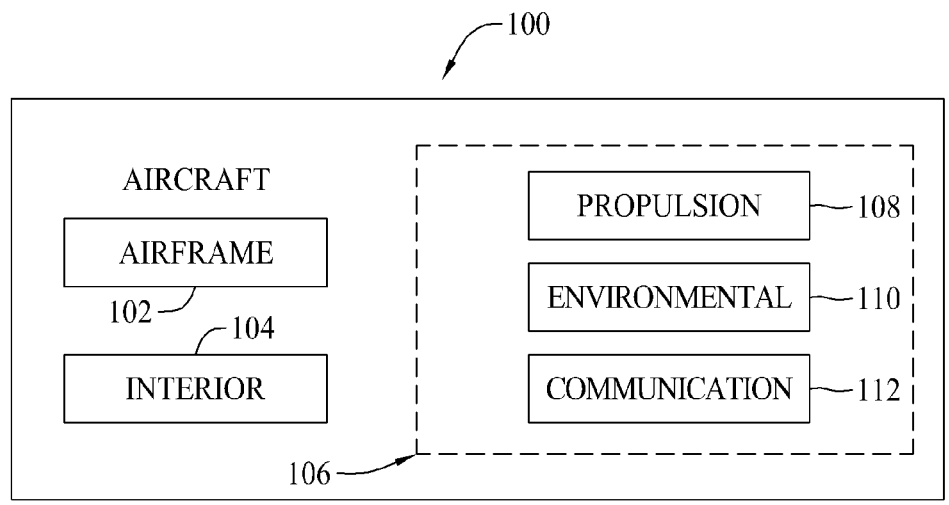
FIG. 1 is a schematic illustration of an exemplary aircraft including a plurality of components.

FIG. 1 illustrates an exemplary aircraft 100 including an airframe 102, an interior 104, and a plurality of operational systems 106. In the exemplary embodiment, interior 104 includes a plurality of objects that have relatively complex geometries, narrow features, and/or crevices. Moreover, the plurality of objects may be fabricated from a plurality of different materials and/or have a variety of different surface textures and/or properties. For example, cabin chairs positioned within interior 104 may have a plurality of crevices, and spaces (cracks) between adjacent chairs may be relatively small. Moreover, the chairs may be fabricated from different materials including fabric, metal, and/or plastic. Interior 104 may include any number of objects having any geometry and/or fabricated from any material that enables aircraft 100 to function as described herein.

In the exemplary embodiment, operational systems 106 include a propulsion system 108 for use in maneuvering aircraft 100, an environmental system 110 for use in detecting and/or controlling an environmental condition, and/or a communication system 112 for use in receiving data and/or information from a remote location (not shown) and/or a passenger entertainment system (not shown) for the care and comfort of passengers. Aircraft 100 may include any number of other systems that enables aircraft 100 to function as described herein.

Figure 2:
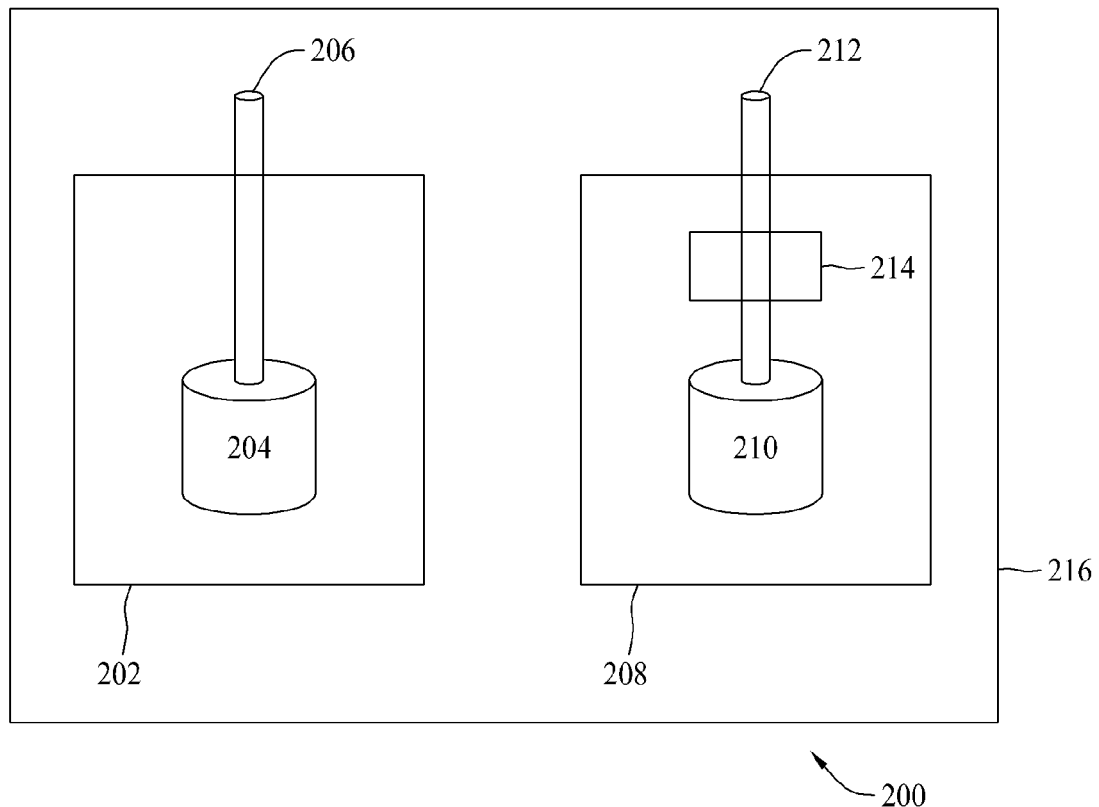
FIG. 2 is a schematic illustration of an exemplary decontamination system that may be used to improve an air quality of the aircraft shown in FIG. 1.

FIG. 2 illustrates an exemplary decontamination system 200 that may be used to facilitate improving an air quality of interior 104. In the exemplary embodiment, system 200 includes a misting device 202 that includes a reservoir 204 and an outlet 206. In the exemplary embodiment, reservoir 204 contains at least one decontaminating agent therein. Moreover, in the exemplary embodiment, misting device 202 is configured to discharge a cloud of small decontaminating droplets (shown in FIG. 4). More specifically, in the exemplary embodiment, fluid used with device 202, such as the decontaminating agent, is discharged from reservoir 204, through outlet 206, and to interior 104.

In the exemplary embodiment, the droplets misted from outlet 206 have a mean diameter of between approximately 0.1 microns and approximately 0.5 microns. In one embodiment, the size of the misted droplets may be variably selected based on at least a viscosity of the decontaminating agent, a desired volatility (i.e., evaporating time) of the decontaminating agent, a temperature within interior 104, and/or the surface and/or object to be decontaminated.

In the exemplary embodiment, system 200 includes a spraying device 208 that includes a reservoir 210 and an outlet 212. More specifically, in the exemplary embodiment, reservoir 210 contains at least one decontaminating agent therein. Moreover, in the exemplary embodiment, spraying device 208 is configured to discharge a stream of decontaminating fluid (shown in FIG. 5) and/or an air stream towards a desired location. More specifically, in the exemplary embodiment, the at least one decontaminating agent is discharged from reservoir 210 through outlet 212 and towards a desired portion of interior 104.

In the exemplary embodiment, the stream discharged from device 208 is formed of droplets having a mean diameter of between approximately 6.0 microns and 20.0 microns. More particularly, in one embodiment, the stream of droplets has a mean diameter of approximately 10.0 microns. In one embodiment, the size of the stream droplets discharged from device 208 may be selected based at least on a viscosity of the decontaminating agent, an ability of the decontaminating agent to retain a charge, a desired volatility (i.e., evaporating time) of the decontaminating agent, a temperature within interior 104, and/or the surface and/or object to be decontaminated.

In the exemplary embodiment, spraying device 208 also includes a charging device 214. Alternatively, charging device 214 may be a separate device from spraying device 208. In the exemplary embodiment, as the decontaminating droplets discharged from device 208 are directed through a relatively large electric field generated by charging device 214, those droplets are subsequently entrained and carried by a selectively targeted stream of air. In the exemplary embodiment, the air stream has a velocity of at least one-half foot per second (0.5 ft/s). More particularly, the air stream has a velocity of at least one foot per second (1.0 ft/s). Alternatively, the air stream may have any suitable velocity that enables system 200 to function as described herein.

In one embodiment, misting device 202 and spraying device 208 are formed in a common housing 216. In such an embodiment, housing 216 is positionable on a stowing cart (not shown) that enables housing 216 to be moved between rows of adjacent chairs spaced along an aisle defined within interior 104. Alternatively, misting device 202 and spraying device 208 may be included separately in a modular system and, in such an embodiment, devices 202 and 208 are in different housings. Moreover, in such an embodiment, misting device 202 is removably coupleable to spraying device 208. In one embodiment, reservoirs 204 and 210 may be a common reservoir. Additionally or alternatively, outlets 206 and 212 may each share a common outlet that is selectively adjustable between a misting configuration and a spraying configuration.

Figure 3:
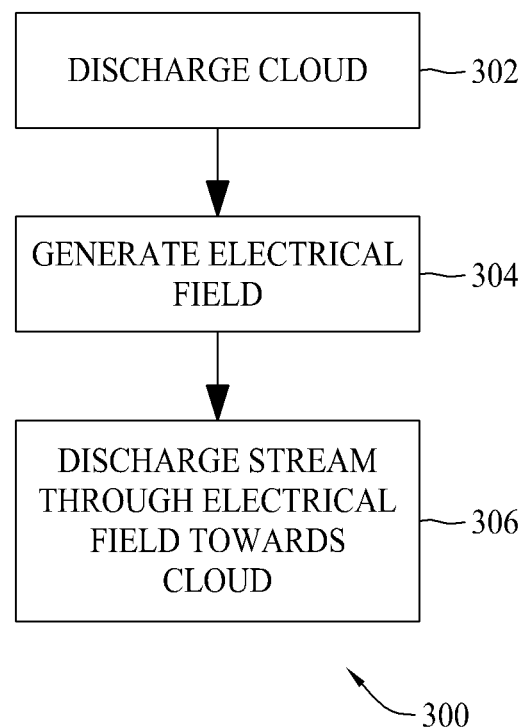
FIG. 3 is a flow chart illustrating an exemplary method that may be used to facilitate improving air quality using the decontamination system shown in FIG. 2.
Figure 4:
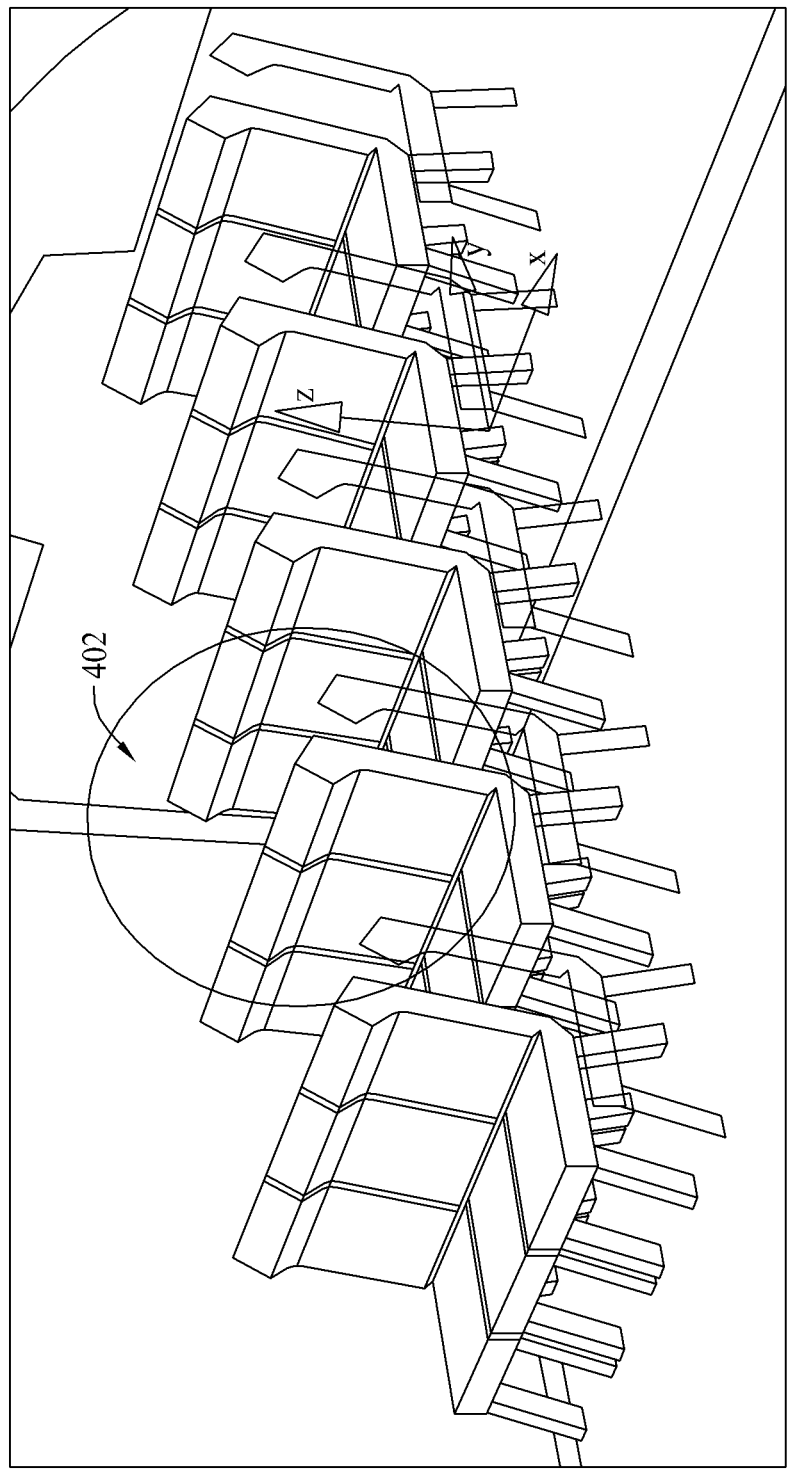
FIGS. 4 and 5 are perspective views of a portion of an interior of the aircraft shown in FIG. 1 in a plurality of exemplary decontamination stages that may occur using the method shown in FIG. 3.

FIG. 3 is a flow chart illustrating an exemplary method 300 that may be used to facilitate improving air quality using decontamination system 200. As shown in FIG. 4, in a first configuration or "mist mode", a relatively large misty cloud 402 of small decontaminating droplets is discharged 302 by misting device 202 into interior 104. In the exemplary embodiment, at least a portion of cloud 402 remains suspended in the air for a predetermined amount of time. More specifically, in the exemplary embodiment, the predetermined amount of time enables cloud 402 to expand to enables a desired amount of area within interior 104 to be covered by cloud 402. In one embodiment, a droplet size is predetermined based on a desired suspension time. Generally, smaller droplets have a longer suspension time than larger droplets.

Figure 5:
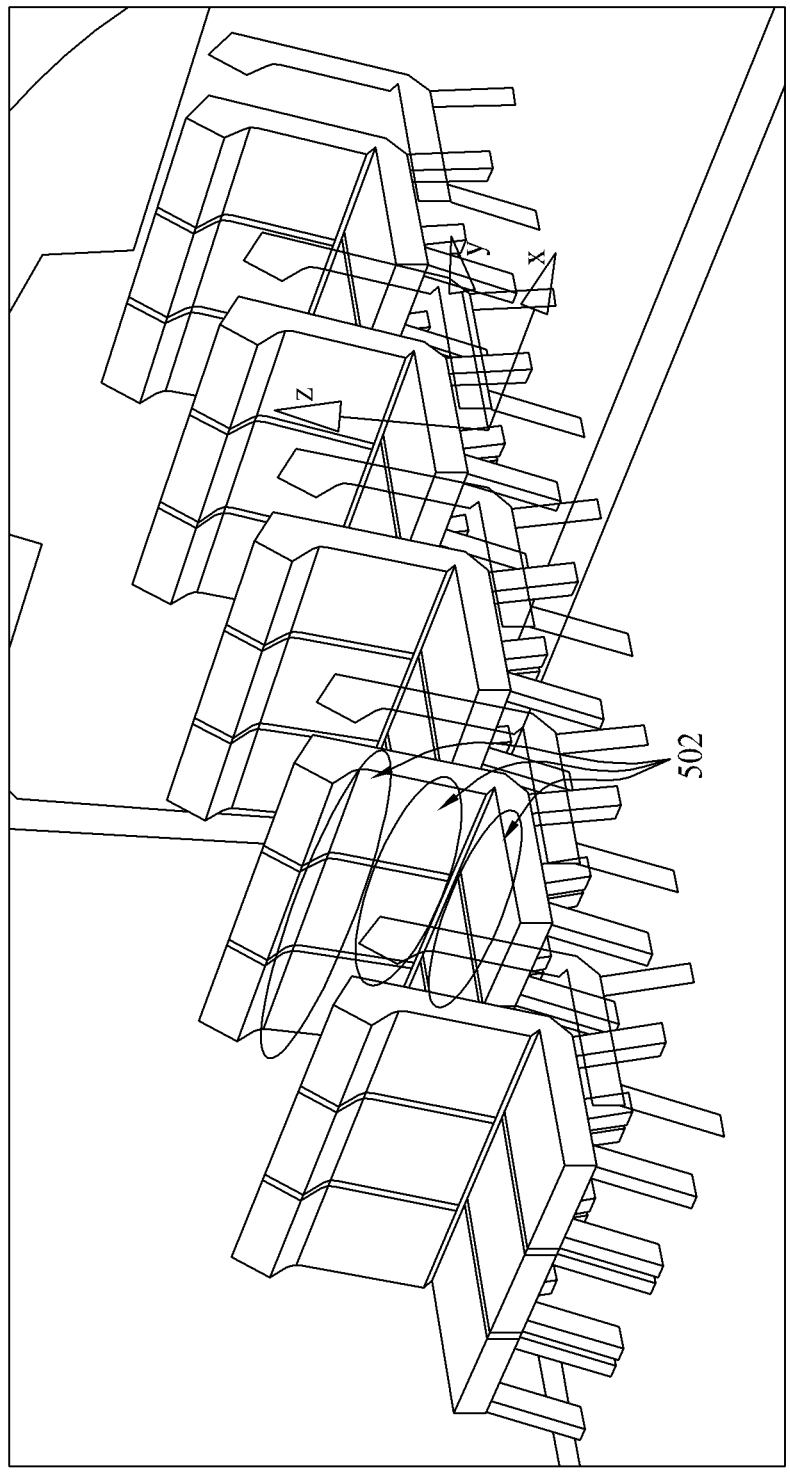

In the exemplary embodiment, charging device 214 generates 304 a relatively large electric field (not shown). As shown in FIG. 5, in a second configuration or "jet mode", a relatively narrow stream 502 of decontaminating droplets are discharged 306 from spraying device 208 through the electric field and into cloud 402. Generally, droplets discharged in the jet mode are "sharper" or have a higher velocity and/or acceleration that droplets discharged in the mist mode. In the exemplary embodiment, stream 502 is selectively directed through cloud 402 and towards a target surface. At least one cloud droplet in the path of stream 502 is charged, thereby enabling the charged droplet to be electrically attracted to the target surface. More specifically, in the exemplary embodiment, stream 502 facilitates shaping cloud 402 using air and/or an electrostatic charge to urge and/or pull at least a portion of cloud 402 onto a desired surface of interior 104 to enable decontaminating agent to be applied to a desired surface and/or object. That is, stream 502 electrically charges the cloud droplets to encourage them to attach to the target surface. Moreover, the charged droplets deposited on the target surface electrically pull the cloud towards the target surface to provide a more complete coverage between the larger stream droplets.

In the exemplary embodiment, each droplet (not shown) in stream 502 is configured to affect a plurality of droplets (not shown) in mist 402. That is, each stream droplet is electronically charged to attract a plurality of mist droplets. In the exemplary embodiment, the electrostatic charge facilitates increasing adhesive properties of the decontaminating agents. Adhesion occurs while stream 502 is in the air charging the cloud and/or after stream 502 is deposited on the target surface. As such, the electrostatic charge facilitates increasing a clinging force associated with the decontaminating agents.

Selectively shaping cloud 402 enables decontaminating agents in stream 502 and/or cloud 402 to be deposited onto a plurality of surfaces within interior 104, including within a crevice and/or relatively small space. Moreover, in the exemplary embodiment, method 300 or, more particularly, the mist mode and/or the jet mode may be repeated to facilitate decontaminating objects that have relatively complex geometries and/or is fabricated from a material that discourages adsorption. As such, the decontamination process may be customized based on at least a type of decontamination liquid, a surface geometry, and/or a surface material.

The subject matter described herein facilitates efficiently and/or reliably decontaminating a desired object and/or surface and, thus, increasing a quality of breathable air within interior 104. Moreover, the subject matter described herein facilitates reducing operating costs associated with aircraft by reducing a decontaminating time of aircraft 100 and/or reducing a likelihood of damage to aircraft 100.

Exemplary embodiments of systems and methods for decontaminating an aircraft are described above in detail. The systems and methods are not limited to the specific embodiments described herein, but rather, components of systems and/or steps of the method may be utilized independently and separately from other components and/or steps described herein. Each component and each method step may also be used in combination with other components and/or method steps. Although specific features of various embodiments may be shown in some drawings and not in others, this is for convenience only. Any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of discharging droplets about at least a portion of an object, said method comprising:
   discharging a cloud including a plurality of cloud droplets in a vicinity of the object, wherein at least some of the plurality of cloud droplets are formed from a decontaminating agent;
   discharging a stream into the cloud after waiting a predetermined amount of time while the plurality of cloud droplets are suspended in air, the stream including a plurality of stream droplets, wherein at least some of the plurality of stream droplets have an electrostatic charge; and
   depositing at least some of the plurality of cloud droplets onto the portion of the object to facilitate decontaminating the portion.

2. A method in accordance with claim 1, wherein discharging a cloud further comprises discharging a cloud, wherein the plurality of cloud droplets have a mean particle size between approximately 0.1 micron and approximately 0.5 micron.

3. A method in accordance with claim 1, wherein discharging a stream further comprises directing the stream such that at least one of the plurality of stream droplets affects a plurality of the cloud droplets.

4. A method in accordance with claim 1, wherein discharging a stream further comprises discharging a stream, wherein at least some of the plurality of stream droplets include a decontaminating agent.

5. A method in accordance with claim 1, wherein discharging a stream further comprises discharging a stream, wherein the plurality of cloud droplets have a mean particle size between approximately 6.0 microns and 20.0 microns.

6. A method in accordance with claim 1 further comprising generating an electric field, wherein the stream is discharged through the electric field.

7. A method of manufacturing a system for use in discharging droplets about at least a portion of an object, said method comprising:
   providing a misting device configured to discharge a cloud formed from a plurality of cloud droplets, wherein at least some of the plurality of cloud droplets include a decontaminating agent; and
   coupling a spraying device to the misting device, the spraying device configured to wait a predetermined amount of time while the plurality of cloud droplets are suspended in air before discharging a stream including a plurality of stream droplets into the cloud, wherein at least some of the plurality of stream droplets have an electrostatic charge.

8. A method in accordance with claim 7 further comprising coupling a charging device to the spraying device, the charging device configured to generate an electric field, wherein the spraying device is oriented to discharge the stream through the electric field.

9. A method in accordance with claim 7 further comprising:
   coupling a reservoir to the misting device and the spraying device such that the misting device and the spraying device are in fluid communication with the reservoir; and
   providing a nozzle that is selectively adjustable between a misting configuration and a spraying configuration.

10. A system for use in discharging droplets about at least a portion of an object, said system comprising:
    a misting device configured to discharge a cloud formed from a plurality of cloud droplets, wherein at least some of the plurality of cloud droplets include a decontaminating agent; and
    a spraying device configured to wait a predetermined amount of time while the plurality of cloud droplets are suspended in air before discharging a stream including a plurality of stream droplets into the cloud, wherein at least some of the plurality of stream droplets have an electrostatic charge, and at least some of the plurality of cloud droplets are deposited on the portion of the object to facilitate decontaminating the portion.

11. A system in accordance with claim 10, wherein the plurality of cloud droplets have a mean particle size between approximately 0.1 micron and approximately 0.5micron.

12. A system in accordance with claim 10, wherein said spraying device is configured to direct the stream such that at least one of the plurality of stream droplets affects a plurality of the cloud droplets.

13. A system in accordance with claim 10, wherein at least some of the plurality of stream droplets include a decontaminating agent.

14. A system in accordance with claim 10, wherein the plurality of cloud droplets have a mean particle size between approximately 6.0 microns and 20.0 microns.

15. A system in accordance with claim 10 further comprising a charging device configured to generate an electric field, wherein the stream is discharged through the electric field.

16. A system in accordance with claim 10 further comprising a housing, wherein said misting device and said spraying device are positionable within said housing.

17. A system in accordance with claim 10 further comprising a reservoir, wherein said misting device and said spraying device are both in fluid communication with said reservoir.

18. A system in accordance with claim 10 further comprising a nozzle that is selectively adjustable between a misting configuration and a spraying configuration.

* * * * *